United States Patent
Ahmed et al.

(10) Patent No.: US 7,811,604 B1
(45) Date of Patent: Oct. 12, 2010

(54) NON-EFFERVESCENT, ORALLY DISINTEGRATING SOLID PHARMACEUTICAL DOSAGE FORMS COMPRISING CLOZAPINE AND METHODS OF MAKING AND USING THE SAME

(75) Inventors: Salah U. Ahmed, New City, NY (US); Lianli Li, St. Louis, MO (US); Tahseen A. Chowdhury, Washington Township, NJ (US)

(73) Assignee: Barr Laboratories, Inc., Woodcliff Lake, NJ (US)

( * ) Notice: Subject to any disclaimer, the term of this patent is extended or adjusted under 35 U.S.C. 154(b) by 649 days.

(21) Appl. No.: 11/598,833

(22) Filed: Nov. 14, 2006

Related U.S. Application Data

(60) Provisional application No. 60/735,832, filed on Nov. 14, 2005.

(51) Int. Cl.
*A61K 9/20* (2006.01)
*A61K 9/14* (2006.01)
*A01N 43/62* (2006.01)

(52) U.S. Cl. .................. 424/465; 424/489; 514/220

(58) Field of Classification Search ............... 424/489, 424/465; 514/220
See application file for complete search history.

(56) References Cited

U.S. PATENT DOCUMENTS

| | | | |
|---|---|---|---|
| 4,084,000 A * | 4/1978 | Fuxe ................... | 514/567 |
| 4,384,005 A | 5/1983 | McSweeney | |
| 4,767,789 A | 8/1988 | Blank et al. | |
| 4,832,956 A | 5/1989 | Gergely et al. | |
| 5,071,646 A | 12/1991 | Malkowska et al. | |
| 5,084,278 A | 1/1992 | Mehta | |
| 5,112,616 A | 5/1992 | McCarty | |
| 5,238,688 A | 8/1993 | Beuving et al. | |
| 5,320,848 A | 6/1994 | Geyer et al. | |
| 5,464,632 A | 11/1995 | Cousin et al. | |
| 5,501,861 A | 3/1996 | Makino et al. | |
| 5,576,014 A | 11/1996 | Mizumoto et al. | |
| 5,587,172 A | 12/1996 | Cherukuri et al. | |
| 5,587,179 A | 12/1996 | Gergely et al. | |
| 5,587,180 A | 12/1996 | Allen et al. | |
| 5,607,697 A | 3/1997 | Alkire et al. | |
| 5,635,210 A | 6/1997 | Allen et al. | |
| 5,725,884 A | 3/1998 | Sherwood et al. | |
| 5,738,875 A | 4/1998 | Yarwood et al. | |
| 5,776,491 A | 7/1998 | Allen et al. | |
| 5,837,285 A | 11/1998 | Nakamichi et al. | |
| 5,837,292 A | 11/1998 | Dijkgraaf et al. | |
| 5,851,553 A | 12/1998 | Myers et al. | |
| 5,866,163 A | 2/1999 | Myers et al. | |
| 5,869,098 A | 2/1999 | Misra et al. | |
| 5,871,778 A * | 2/1999 | Kino et al. ................. | 424/489 |
| 5,876,759 A | 3/1999 | Gowan | |
| 5,939,091 A * | 8/1999 | Eoga et al. ................. | 424/441 |
| 5,955,107 A | 9/1999 | Augello et al. | |
| 5,958,453 A | 9/1999 | Ohno et al. | |
| 6,024,981 A | 2/2000 | Khankari et al. | |
| 6,066,337 A | 5/2000 | Allen et al. | |
| 6,083,531 A | 7/2000 | Humbert-Droz et al. | |
| 6,106,861 A | 8/2000 | Chauveau et al. | |
| 6,106,865 A | 8/2000 | Staniforth et al. | |
| 6,149,938 A | 11/2000 | Bonadeo et al. | |
| 6,156,339 A | 12/2000 | Grother et al. | |
| 6,165,512 A | 12/2000 | Mezaache et al. | |
| 6,177,104 B1 | 1/2001 | Allen et al. | |
| 6,224,909 B1 | 5/2001 | Opitz et al. | |
| 6,284,270 B1 | 9/2001 | Lagoviyer et al. | |
| 6,316,029 B1 | 11/2001 | Jain et al. | |
| 6,328,994 B1 | 12/2001 | Shimizu et al. | |
| 6,368,625 B1 | 4/2002 | Siebert et al. | |
| 6,375,982 B1 | 4/2002 | Cherukuri | |
| 6,465,009 B1 | 10/2002 | Liu et al. | |
| 6,465,010 B1 | 10/2002 | Lagoviyer et al. | |
| 6,586,004 B2 | 7/2003 | Shimizu et al. | |
| 6,589,556 B2 | 7/2003 | Cherukuri | |
| 6,656,492 B2 | 12/2003 | Kajiyama et al. | |
| 6,669,957 B1 | 12/2003 | Laruelle et al. | |
| 6,680,071 B1 | 1/2004 | Johnson et al. | |
| 6,723,348 B2 | 4/2004 | Faham et al. | |
| 6,740,339 B1 | 5/2004 | Ohkouchi et al. | |
| 6,740,341 B1 | 5/2004 | Holt et al. | |

(Continued)

FOREIGN PATENT DOCUMENTS

AU  200029224 B2  9/2000

(Continued)

OTHER PUBLICATIONS

Bi, Y.X., et al., "Preparation and evaluation of a compressed tablet rapidly disintegrating in the oral Cavity," *Chem. Pharm. Bull.* 44:2121-2127, Pharmaceutical Society of Japan (1996).

(Continued)

*Primary Examiner*—Johann R Richter
*Assistant Examiner*—Danielle Sullivan
(74) *Attorney, Agent, or Firm*—Sterne, Kessler, Goldstein & Fox P.L.L.C.

(57) ABSTRACT

The present invention is directed to non-effervescent, orally disintegrating dosage forms comprising free base clozapine that are substantially free of acids, water-soluble polymers, taste-masking polymers, and coatings, and methods of making and using the same.

29 Claims, 1 Drawing Sheet

U.S. PATENT DOCUMENTS

| | | | |
|---|---|---|---|
| 7,067,116 | B1 | 6/2006 | Bess et al. |
| 2001/0010825 | A1 | 8/2001 | Shimizu et al. |
| 2002/0034540 | A1 | 3/2002 | Price |
| 2002/0049233 | A1 | 4/2002 | Kararli et al. |
| 2002/0071864 | A1 | 6/2002 | Kim et al. |
| 2002/0160043 | A1 | 10/2002 | Coleman |
| 2003/0017202 | A1 | 1/2003 | Bunick et al. |
| 2003/0026835 | A1 | 2/2003 | Nishii et al. |
| 2003/0035833 | A1 | 2/2003 | He |
| 2003/0035839 | A1 | 2/2003 | Hirsh et al. |
| 2003/0054038 | A1 | 3/2003 | Crew et al. |
| 2003/0099701 | A1 | 5/2003 | Takaishi et al. |
| 2003/0104063 | A1 | 6/2003 | Babcock et al. |
| 2003/0104066 | A1 | 6/2003 | Murai et al. |
| 2003/0124184 | A1 | 7/2003 | Mezaache et al. |
| 2003/0147948 | A1 | 8/2003 | Shinoda et al. |
| 2003/0165566 | A1 | 9/2003 | O'Toole et al. |
| 2003/0170309 | A1 | 9/2003 | Babcock et al. |
| 2003/0220413 | A1 | 11/2003 | Petereit et al. |
| 2003/0229027 | A1 | 12/2003 | Eissens et al. |
| 2004/0014680 | A1 | 1/2004 | Nakagami et al. |
| 2004/0022849 | A1 | 2/2004 | Castan et al. |
| 2004/0033258 | A1 | 2/2004 | Koike |
| 2004/0037882 | A1 | 2/2004 | Johnson et al. |
| 2004/0122106 | A1 | 6/2004 | Ohta et al. |
| 2004/0253307 | A1 | 12/2004 | Hague et al. |
| 2004/0265375 | A1 | 12/2004 | Platteeuw et al. |
| 2005/0013857 | A1 | 1/2005 | Fu et al. |
| 2005/0036977 | A1 | 2/2005 | Gole et al. |
| 2005/0089568 | A1 | 4/2005 | Oshlack et al. |
| 2005/0106240 | A1 | 5/2005 | Tanaka et al. |
| 2005/0112196 | A1 | 5/2005 | Xie et al. |
| 2005/0123609 | A1 | 6/2005 | Hirsh et al. |
| 2005/0163830 | A1 | 7/2005 | Rademacher et al. |
| 2005/0181050 | A1 | 8/2005 | Hirsh et al. |
| 2005/0186284 | A1 | 8/2005 | Yang et al. |
| 2005/0208127 | A1 | 9/2005 | Ogasawara et al. |
| 2005/0208141 | A1 | 9/2005 | Farber et al. |
| 2005/0232988 | A1 | 10/2005 | Venkatesh et al. |
| 2005/0266088 | A1 | 12/2005 | Hinrichs et al. |

FOREIGN PATENT DOCUMENTS

| | | | |
|---|---|---|---|
| EP | 1 161 941 A1 | 12/2001 | |
| WO | WO 87/05804 | 10/1987 | |
| WO | WO 98/53798 | 12/1998 | |
| WO | WO 99/43306 | 9/1999 | |
| WO | WO 03/072084 A1 | 9/2003 | |
| WO | WO 03/103629 A1 | 12/2003 | |

OTHER PUBLICATIONS

Bi, Y.X., et al., "Evaluation of rapidly disintegrating tablets prepared by a direct compression method," *Drug Dev. Ind. Pharm.* 25:571-581, Marcel Dekker, Inc. (1999).

Bogner, R. and Wilkosz, M., "Fast-dissolving Tablets," *U.S. Pharmacist* 27:34-43, Jobson Medical Information, LLC (2002) Accessed online: http://www.uspharmacist.com/oldformat.asp?url=newlook/files/feat/fastdissolving.htm, last.accessed Sep. 27, 2006.

Borsadia, S.B. et al., "Quick-dissolving films—a novel approach to drug delivery" *Drug Delivery Tech.* 3, Drug Delivery Technology (2003) Accessed online: http://www.drugdeliverytech.com/cgi-bin/articles.cgi?idArticle=138, last accessed Sep. 27, 2006.

Brown, D. "Orally disintegrating tablets—taste over speed," *Drug Delivery Tech.* 3, Drug Delivery Technology (2003) Accessed online: http://www.drugdeliverytech.com/cgi-bin/articles.cgi?idArticle=164, last accessed Sep. 27, 2006.

Dobetti, L., "Fast-melting tablets: developments and technologies," *Pharm. Tech.: Drug Delivery* 2001:44-50, Advanstar Communications, Inc. (2001) Accessed online: http://www.pharmtech.com/pharmtech/data/articlestandard/pharmtech/512001/5137/article.pdf, last accessed Sep. 27, 2006.

El-Arini, S.K. and Clas, S.D., "Evaluation of disintegration testing of different fast dissolving tablets using the texture analyzer," *Pharm. Dev. Technol.* 7:361-371, Marcel Dekker, Inc. (2002).

Habib, W., et al., "Fast-dissolve drug delivery systems," *Critical Reviews™ in Therapeutic Drug Carrier Systems* 17:61-72, Begell House, Inc. (2000).

Ishikawa, T., et al., "Preparation of rapidly disintegrating tablet using new types of microcrystalline cellulose (PH-M Series) and low sub-stituted-hydroxypropylcellulose or spherical sugar granules by direct compression method," *Chem. Pharm. Bull.* 49:134-139, Pharmaceutical Society of Japan (2001).

Klancke, J. "Dissolution testing of orally disintegrating tablets," *Dissolution Tech.* 10, Dissolution Technologies, Inc. (2003) Accessed online: http://www.dissolutiontech.com/DTresour/0503art/DT0503art1.pdf, last accessed Sep. 27, 2006.

Koizumi, K., et al., "New method of preparing high-porosity rapidly saliva soluble compressed tablets using mannitol with camphor, a subliming material," *Intl. J. Pharm.* 152:127-131, Elsevier Science B.V. (1997).

Liang, A.C. and Chen, L.H., "Fast-dissolving intraoral drug delivery systems," *Expert Opinion on Therapeutic Patents* 11:981-986, Ashley Publications Ltd. (2001).

Lowenthal, W., "Mechanism of action of tablet disintegrants," *Pharmaceutica Acta Helvetiae* 48:589-609, Elsevier B.V. (1973).

Massimo, G., et al., "Disintegration propensity of tablets evaluated by means of disintegrating force kinetics," *Pharm. Dev. Technol.* 5:163-169, Marcel Dekker, Inc. (2000).

Ringard, J. and Gyuot-Hermann, A.M., "Calculation of disintegrant critical concentration in order to optimize tablets disintegration," *Drug Dev. Ind. Pharm.* 14:2321-2339, Marcel Dekker, Inc. (1988).

Sastry, S.V., et al., "Recent technological advances in oral drug delivery—a review," *Pharm. Sci. Technol. Today* 3:138-145, Elsevier Science (2000).

Watanabe, Y., et al., "New compressed tablet rapidly disintegrating in saliva in the mouth using crystalline cellulose and a disintegrant," *Biol. Pharm. Bull.* 18:1308-1310, Pharmaceutical Society of Japan (1995).

Mirtazapine Orally Disintegrating Tablets, The Electronic Orange Book, The United State Food and Drug Administration (15 mg and 30 mg, Dec. 2003; 45 mg, Feb. 2006) Accessed online: http://www.accessdata.fda.gov/scripts/cder/ob/docs/obdetail.cfm?Appl_No=076307&TABLE1=OB_Rx, last accessed: Sep. 27, 2006.

Label and Packaging for Mirtazapine Orally Disintegrating Tablets (15 mg and 30 mg), Barr Laboratories, Inc. (2003).

Ahmed et al., U.S. Appl. No. 10/902,836, filed Aug. 2, 2004 (not published).

Ahmed et al., U.S. Appl. No. 10/923,021, filed Aug. 23, 2004 (not published).

Ahmed et al., U.S. Appl. No. 11/048,120, filed Feb. 2, 2005 (not published).

Ahmed et al., U.S. Appl. No. 11/440,449, May 25, 2006 (not published).

Ahmed et al., U.S. Appl. No. 11/441,458, filed May 25, 2006 (not published).

Ahmed et al., U.S. Appl. No. 11/441,459, filed May 25, 2006 (not published).

Ahmed et al., U.S. Appl. No. 11/446,508, filed Jun. 3, 2006 (not published).

Ahmed et al., U.S. Appl. No. 11/478,299, filed Jun. 30, 2006 (not published).

Ahmed et al., U.S. Appl. No. 11/498,265, filed Aug. 3, 2006 (not published).

Ahmed et al., U.S. Appl. No. 11/498,266, filed Aug. 3, 2006 (not published).

\* cited by examiner

NON-EFFERVESCENT, ORALLY DISINTEGRATING SOLID PHARMACEUTICAL DOSAGE FORMS COMPRISING CLOZAPINE AND METHODS OF MAKING AND USING THE SAME

CROSS REFERENCE TO RELATED APPLICATIONS

This application claims the benefit of the filing date of U.S. Appl. No. 60/735,832, filed Nov. 14, 2005, which is incorporated by reference herein in its entirety.

BACKGROUND OF THE INVENTION

1. Field of the Invention

The present invention relates to non-effervescent, orally disintegrating pharmaceutical dosage forms suitable for administering free base clozapine to a subject in need thereof, and methods of making and using the same.

2. Related Art

Clozapine, an atypical antipsychotic agent, is commonly prescribed for the management and symptomatic relief from the symptoms of severe schizophrenia. Clozapine is a selective monoaminergic antagonist with high affinity for the serotonin Type 2 ($5HT_2$), dopamine Type 2 ($D_2$), 1 and 2 adrenergic, and $H_1$ histaminergic receptors, and can also be used for treating various dopamine-mediated behaviors. However, due to the risk of side effects that include agranulocytosis, hyperglycemia, hypertriglyceridemia, and increased appetite, patients are typically only prescribed clozapine after more conventional treatments (e.g., chlorpromazine or haloperidol) have proven inadequate.

Clozapine is presently available in oral tablet and orally disintegrating tablet dosage forms (e.g., FAZACLO® 25, 50 and 100 mg orally disintegrating tablets, Alamo Pharmaceuticals, LLC, Beverly Hills, Calif.). Orally disintegrating tablets can be preferred for dosage forms for patients suffering from schizophrenia because they can be taken without water intake and disintegrate immediately upon contacting the tongue or buccal cavity, thereby improving patient compliance.

However, during clinical trials patients have complained of a bitter taste when administered orally disintegrating tablets containing clozapine. While the free base form of clozapine is tasteless, the acid addition salt of clozapine is bitter tasting. An acid contained within an effervescent orally disintegrating tablet can react with free base clozapine during storage, thereby exacerbating its bitter taste. Thus, effervescent clozapine orally disintegrating dosage forms (that contain an acid as part of an effervescent couple) typically include a protective polymer coating surrounding the free base clozapine granules (see, e.g., U.S. Pat. Nos. 5,178,878 and 6,024,981). The need to apply a polymer coating to free base clozapine granules adds unwanted cost and time to the manufacturing process. Moreover, the fragility of a polymer coating around the free base clozapine granules requires that limited compression force be used during tableting to avoid damaging the polymer coating, and thereby adding challenges into product handling and packaging.

BRIEF SUMMARY OF THE INVENTION

The present invention is directed to non-effervescent, orally disintegrating solid pharmaceutical dosage forms comprising a substantially homogeneous compressed dry mixture comprising:
(a) free base clozapine;
(b) a non-polymeric, water-soluble carrier; and
(c) a disintegrant in a concentration of about 20% to about 60% by weight of the dosage forms;

wherein the dry mixture and pharmaceutical dosage forms are substantially free of: acids, water-soluble polymers, taste-masking polymers, and coatings, and wherein the dosage forms disintegrate in about 60 seconds or less.

The present invention is also directed to a method of treating schizophrenia or dopamine mediated behaviors comprising administering non-effervescent, orally disintegrating solid pharmaceutical dosage forms to a subject in need thereof, wherein the pharmaceutical dosage forms comprise: a substantially homogeneous compressed dry mixture comprising:
(a) free base clozapine;
(b) a non-polymeric, water-soluble carrier; and
(c) a disintegrant in a concentration of about 20% to about 60% by weight of the dosage forms;

wherein the dry mixture and pharmaceutical dosage forms are substantially free of: acids, water-soluble polymers, taste-masking polymers, and coatings, and wherein the dosage forms disintegrate in about 60 seconds or less.

The present invention is also directed to a process of preparing non-effervescent, orally disintegrating solid pharmaceutical dosage forms, the process comprising:
(a) dry mixing:
(i) free base clozapine,
(ii) a non-polymeric, water-soluble carrier, and
(iii) a disintegrant, to form a dry mixture, wherein the disintegrant is present in a concentration of about 20% to about 60% by weight of the dry mixture; and (b) compressing the dry mixture to form the pharmaceutical dosage forms, wherein the dry mixture is substantially free of: acids, water-soluble polymers, taste-masking polymers, and coatings, and wherein the dosage forms disintegrate in about 60 seconds or less.

The present invention is also directed to a pharmaceutical dosage form prepared by the above process.

In some embodiments, the free base clozapine is present in a concentration of about 10% to about 30% by weight of the dosage forms.

In some embodiments, the free base clozapine has a particle size $D_{50}$ of about 20 μm or less, and/or a particle size $D_{90}$ of about 50 μM or less.

Non-polymeric, water-soluble carriers suitable for use with the present invention include, but are not limited to, arabinose, dextrose, erythritol, fructose, galactose, inositol, lactitol, maltitol, maltose, mannitol, sorbitol, sucrose, tagatose, trehalose, xylitol, and combinations thereof.

In some embodiments, the non-polymeric, water-soluble carrier is present in a concentration of about 20% to about 60% by weight of the dosage forms.

Disintegrants suitable for use with the present invention include crospovidone, croscarmellose sodium, sodium starch glycolate, and combinations thereof.

In some embodiments, the pharmaceutical dosage forms further comprise: a hydrophilic, water-insoluble polymer.

In some embodiments, the pharmaceutical dosage forms further comprise: a flavorant and a sweetener in a concentration of about 7% to about 30% by weight of the dosage forms.

In some embodiments, the pharmaceutical dosage forms have a pH of about 6.5 to about 8.

In some embodiments, the process further comprises: adding to the dry mixture a flavorant and a sweetener in a concentration of about 7% to about 30% by weight of the dry mixture.

DETAILED DESCRIPTION OF THE INVENTION

Figure 1:
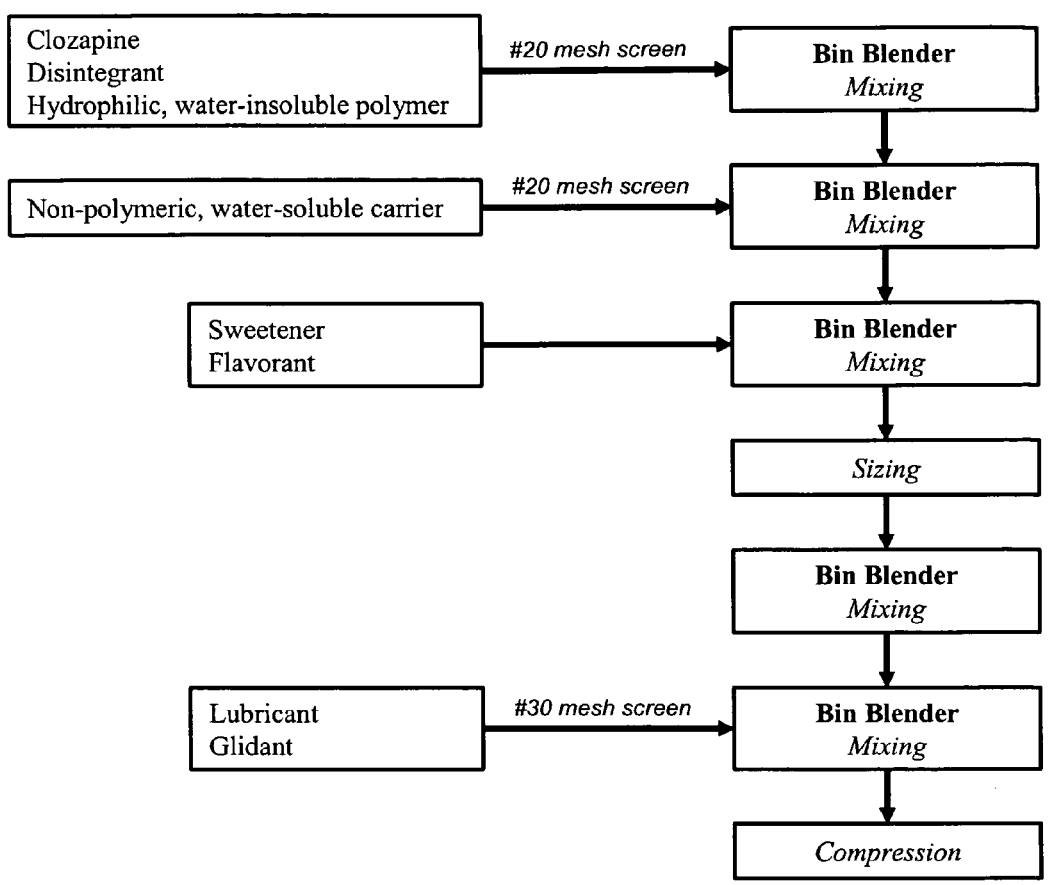
FIG. 1 is a process flow chart representing a process of preparing the non-effervescent, orally disintegrating solid pharmaceutical dosage forms of the present invention.

The present invention is directed to non-effervescent, orally disintegrating solid pharmaceutical dosage forms comprising free base clozapine and a combination of excipients that result in rapid disintegration of the solid dosage forms to form a solution and/or particulate mass that can be easily swallowed without water intake by a subject in need thereof. The pharmaceutical dosage forms of the present invention exhibit excellent taste characteristics and provide safe, effective absorption and high bioavailability of clozapine, and are particularly useful for treating schizophrenia and the symptoms thereof.

The chemical name for clozapine is 8-chloro-11-(4-methyl-1-piperazinyl)-5H-dibenzo[b,e][1,4]diazepine. Free base clozapine has the following chemical structure:

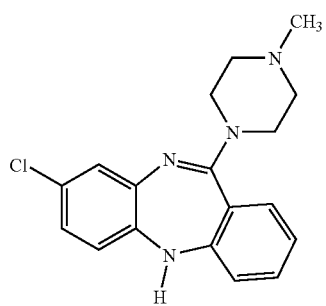

As used herein, "free base clozapine" refers to hydrates, solvates and prodrugs of the free base form of clozapine. Clozapine for use with the present invention does not include salts of clozapine such as acid addition salts. The free base clozapine formulations of the present invention also include both racemic mixtures as well as enantiomerically pure forms of free base clozapine.

Throughout the present disclosure, all expressions of percentage, ratio, corporation, and the like are "by weight" unless otherwise indicated. As used herein, "by weight" is synonymous with the term "by mass," and indicates that a ratio or percentage defined herein is done according to weight rather than volume, thickness, or some other measure.

As used herein, the term "about," when used in conjunction with a percentage or other numerical amount, means plus or minus 10% of that percentage or other numerical amount. For example, the term "about 80%," would encompass 80% plus or minus about 8%.

Non-Effervescent, Orally Disintegrating Solid Pharmaceutical Dosage Forms

The present invention is directed to non-effervescent, orally disintegrating solid pharmaceutical dosage forms comprising a substantially homogeneous compressed dry mixture comprising:

(a) free base clozapine;
(b) a non-polymeric, water-soluble carrier; and
(c) a disintegrant in a concentration of about 20% to about 60% by weight of the dosage forms;

wherein the dry mixture and pharmaceutical dosage forms are substantially free of: acids, water-soluble polymers, taste-masking polymers, and coatings, and wherein the dosage forms disintegrate without effervescence within the buccal cavity without water intake in about 60 seconds or less.

As used herein, "solid pharmaceutical dosage form" refers to a tablet, wafer, film, powder, dragee, or hard or soft gelatin capsule. In some embodiments, the dosage forms of the present invention are tablets. As used herein, the term "tablet" refers to uncoated compressed pharmaceutical dosage forms of all shapes and sizes. The solid dosage forms of the present invention can have a substantially rigid structure, which is mechanically stable and robust, with a low friability. A "unit dosage" is that amount of the pharmaceutical composition that is individually administered.

The net weight of the pharmaceutical dosage forms of the present invention is about 50 mg to about 1000 mg, about 50 mg to about 500 mg, about 50 mg to about 480 mg, about 50 mg to about 360 mg, about 50 mg to about 240 mg, about 50 mg to about 180 mg, or about 50 mg to about 150 mg. In some embodiments, the pharmaceutical dosage forms of the present invention weigh about 100 mg, about 120 mg, about 150 mg, about 180 mg, about 240 mg, about 300 mg, about 360 mg, or about 450 mg.

In some embodiments, as the unit dosage amount of clozapine varies, the weight of the pharmaceutical dosage forms increases or decreases in a proportional manner (i.e., "dose-proportional" dosage forms). In some embodiments, the weight of the pharmaceutical dosage form is constant as the unit dosage amount of clozapine varies (i.e., "dose-similar" dosage forms). Dose-similar tablets can be particularly useful because higher doses of clozapine can be delivered using small tablets.

As used herein, an "orally disintegrating" dosage form refers to solid dosage forms containing free base clozapine that "disintegrate rapidly, usually within a matter of seconds, when placed upon the tongue." As used herein, "orally disintegrating" also refers to disintegration within the buccal cavity of a subject without water intake in about 60 seconds or less. Additionally, "orally disintegrating" can refer to a loss of structural integrity by the dosage forms upon their placement in the buccal cavity of a subject, thereby forming a particulate, viscous, or liquid composition that can be easily swallowed without water intake. "Disintegrating" also refers to the loss of integrity of the dosage forms of the present invention to form granules, aggregates or particles, as generally described in Remington: The Science and Practice of Pharmacy, 21st Ed., Lippincott Williams & Wilkins, Baltimore, Md. (2003), which is incorporated herein by reference in its entirety.

In some embodiments, the dosage forms of the present invention disintegrate in the buccal cavity of a human subject without water intake in about 60 seconds or less, about 45 seconds or less, about 30 seconds or less, about 15 seconds or less, about 10 seconds or less, or about 5 seconds or less. In some embodiments, the pharmaceutical dosage forms of the present invention disintegrate the buccal cavity of a human subject without water intake in about 5 seconds to about 60 seconds, about 5 seconds to about 45 seconds, about 5 seconds to about 30 seconds, about 5 seconds to about 15 seconds, about 5 seconds to about 10 seconds, or about 5 seconds to about 8 seconds.

As used herein, "dissolution" refers to the process by which the free base clozapine goes into solution from the solid dosage forms of the invention. In some embodiments, at least about 75%, at least about 80%, at least about 85%, or at least about 90% of the free base clozapine contained in a dosage forms of the present invention dissolves within about 30 minutes in 900 mL of 0.1 N HCl at a paddle speed of 50 rpm.

As used herein, "hardness" refers to the degree of force (in kilograms, pounds, kiloponds, mohls or arbitrary units) required to break apart a solid dosage form of the present invention.

As used herein, "friability" refers to the tendency of a solid dosage form to crumble upon placement in a rotating apparatus known as a friabilator.

As used herein, "substantially homogeneous" refers to the mixtures, compositions, or dosage forms of the present invention having a substantially uniform distribution of ingredients throughout (i.e., the solid dosage forms of the present invention do not have a composition gradient or a laminate structure).

The dosage forms of the present invention are produced by compression, and are compressed dosage forms. "Compressed" refers to a mixture or composition that has been compacted under pressure. A compressed composition has a density greater than that of the composition prior to compression. The compressed composition can also have a different shape than the composition prior to compression. The dosage forms of the present invention can be prepared by any method of compression known by those skilled in the art of producing compressed dosage forms.

As used herein, "composition" and "mixture" are used interchangeably and refer to a combination of two or more substances.

As used herein, a "therapeutically effective" amount of clozapine refers to an amount of free base clozapine that produces the desired therapeutic response upon oral administration according to a single or multiple dosage regimen. For example, a therapeutically effective amount for treating schizophrenia or a related condition refers to the amount that, when administered, diminishes one or more symptoms associated with this condition. The precise dosage of clozapine necessary to be therapeutically effective will vary with age, size, sex and condition of the subject, and the nature and severity of the disorder, disease, or condition to be treated. Thus, in some embodiments a precise therapeutically effective amount cannot be specified in advance, but can be determined by a caregiver using, for example, dose titration or by routine experimentation with an animal model.

A therapeutically effective dosage of free base clozapine for use with the present invention is about 12.5 mg to about 900 mg per day, about 25 mg to about 900 mg per day, about 50 mg to about 900 mg per day, about 100 mg to about 900 mg per day, about 300 mg to about 900 mg per day, about 100 mg to about 600 mg per day, about 300 mg to about 600 mg per day, or about 300 mg to about 400 mg per day.

The pharmaceutical dosage forms of the present invention comprise free base clozapine in a concentration of about 10% to about 30%, about 10% to about 25%, about 10% to about 20%, about 15% to about 30%, about 15% to about 25%, about 15%, about 20%, or about 17% by weight of the dosage forms.

Clozapine for use with the present invention has a particulate morphology. As use herein, a "particulate" refers to clozapine, excipients, and mixtures and compositions thereof that are composed of discrete particles.

As used herein, the term "particle size" refers to particle diameter. Particle size and particle size distribution can be measured using, for example, a Hyac/Royco particle size analyzer, a Malvern particle size analyzer, a Beckman Coulter laser diffraction particle size analyzer, or a Shimadzu laser diffraction particle size analyzer. As used herein, the term "diameter" relates to a volumetric measurement based on an approximate spherical shape of a particle. In addition to encompassing free base clozapine particles of a given size, the present invention is also directed to formulations and solid oral dosage forms wherein the distribution of particle sizes of free base clozapine and the excipients are controlled. As used herein, a "distribution" refers to the number or concentration (i.e., percentage) of particles having a certain size, or range of sizes, within a given lot, batch, or solid oral dosage form of the present invention.

As used herein, "volume mean diameter," when used in reference to the size of particles for use with the present invention, refers to the value of the volume moment mean as represented by D[4,3]. This value indicates the central point of frequency around which the distribution of surface area or volume rotates.

As used herein, a "mean" value, when used in reference to the diameter of particles refers to the sum of the size measurements of all measurable particles measured divided by the total number of particles measured. For example, for five measurable particles that could be measured, and were determined to have diameters of 20 µm, 23 µm, 20 µm, 28 µm and 19 µm, the mean diameter would be 22 µm.

As used herein, the term "median," when used in reference to the diameter of particles indicates that about 50% of all measurable particles have a particle size equal to or less than the defined median particle size value, and that about 50% of all measurable particles measured have a particle size greater than the median particle size value. As used herein, the "median" particle size is synonymous with the "particle size $D_{50}$," in microns. For example, for the five particle values listed above, the median diameter, or particle size $D_{50}$, would be 20 µm.

As used herein, "particle size $D_{90}$," refers a mixture wherein about 90% of all measurable particles have a diameter equal to or less than the value $D_{90}$, in microns, and 10% of the measurable particles have a diameter greater than the value of $D_{90}$, in microns.

As used herein, the term "mode," when used in reference to the size of particles indicates the most frequently-occurring particle size value. For example, for the five particle values listed above, the mode diameter would be 50 µm. In some embodiments, free base clozapine particles of the present invention can have a mono-modal particle size distribution (i.e., have a single mode value). In some embodiments, free base clozapine particles of the present can have a multi-modal particle size distribution (i.e., have more than one mode value).

In some embodiments, free base clozapine for use with the present invention has a particle size $D_{50}$ of about 20 µm or less, about 18 µm or less, about 15 µm or less, about 12 µm or less, about 7 µm or less, or about 5 µm or less. In some embodiments, particulate free base clozapine for use with the present invention has a $D_{50}$ of about 1 µm to about 20 µm, about 1 µm to about 18 µm, about 1 µm to about 15 µm, about 1 µm to about 12 µm, about 1 µm to about 10 µm, about 1 µm to about 7 µm, about 1 µm to about 5 µm, about 5 µm to about 20 µm, about 5 µm to about 18 µm, about 5 µm to about 15 µm, or about 10 µm to about 20 µm.

In some embodiments, free base clozapine for use with the present invention has a particle size $D_{90}$ of about 50 µm or less, about 40 µm or less, about 30 µm or less, or about 20 µm or less. In some embodiments, particulate free base clozapine for use with the present invention has a $D_{90}$ of about 10 µm to about 50 µm, about 10 µm to about 40 µm, about 10 µm to about 30 μm, about 10 μm to about 20 μm, about 20 μm to about 50 μm, or about 30 μm to about 50 μm.

The dosage forms of the present invention also comprise one or more pharmaceutically acceptable excipients. As used herein, "pharmaceutically acceptable" refers to those excipients, compounds, materials, and/or compositions that are, within the scope of sound medical judgment, suitable for contact with the tissues of human beings and animals without excessive toxicity, irritation, allergic response, or other possible complications commensurate with a reasonable benefit/risk ratio. As used herein, the term "excipient" refers to the substances useful for combining with free base clozapine to provide a solid dosage form suitable for administering to a subject in need thereof. In addition, one of skill in the art will recognize that pharmaceutically acceptable excipients can be used in the present invention including those listed in *The Handbook of Pharmaceutical Excipients*, 5th Ed., The Pharmaceutical Press and American Pharmacists Association, London, UK and Washington, D.C. (2006) and *Remington: The Science and Practice of Pharmacy*, Lippincott Williams & Wilkins, 21st Ed. (2005), which are incorporated herein by reference in their entirety.

Useful pharmaceutically acceptable excipients include those that impart good flow and compression characteristics to a dry composition that is then compressed. Pharmaceutically acceptable excipients and additives suitable for use with the present invention include, but are not limited to, non-polymeric water-soluble carriers; disintegrants; binders; inorganic excipients; lubricants; glidants; sweeteners; flavorants; and combinations thereof.

The pharmaceutical dosage forms of the present invention comprise a non-polymeric water-soluble carrier. As used herein, "water-soluble" refers to an excipient having a solubility of at least 1 part in 10 parts of water at 25° C. (i.e., a water solubility of at least 10% by weight). As used herein, "non-polymeric" refers to molecular and oligomeric carriers having a structure comprising about 10 repeat units or less (i.e., carbohydrates comprising 10 or less glycosidic residues). In some embodiments, a non-polymeric water-soluble carrier has a molecular weight of about 500 Daltons or less. In some embodiments, a non-polymeric water-soluble carrier has a heat of solution of about –200 J/g to about 55,000 J/g. In some embodiments, a non-polymeric water-soluble carrier comprises a non-reducing sugar (i.e., a sugar lacking a glycosidic hydroxyl group or a sugar that is incapable of reacting with a basic nitrogen functional group in a Maillard-type reaction).

Non-polymeric water-soluble carriers suitable for use with the present invention include, but are not limited to, arabinose, dextrose, erythritol, fructose, galactose, inositol, lactitol, maltitol, maltose, mannitol (e.g., PARTECK® M-200, available from Merck KGaA, Darmstadt, Fed. Rep. Germany, and PEARLITOL® SD-200, SD-300 and SD-400, available from Roquette America Inc., Keokuk, Iowa), sorbitol, sucrose, tagatose, trehalose, xylitol (e.g., XYLISORB® 300, available from Roquette America Inc., Keokuk, Iowa), and combinations thereof. As used herein, "inositol" refers to any one of the isomers of inositol, including myo-inositol, the major nutritionally active form of inositol.

A non-polymeric water-soluble carrier is present in the pharmaceutical dosage forms of the present invention in a concentration of about 1% to about 10%, about 3% to about 10%, about 3% to about 7%, about 20% to about 60%, about 30% to about 60%, about 40% to about 60%, about 20% to about 50%, about 30% to about 50%, about 40% to about 50%, about 42%, or about 46% by weight of the dosage forms.

The pharmaceutical dosage forms of the present invention do not require effervescence to disintegrate in water, but instead rely upon disintegrant to facilitate their disintegration in the buccal cavity. In some embodiments, a disintegrant comprises a hydrophilic, water-insoluble polymer. Disintegrants suitable for use with the present invention include, but are not limited to, cross-linked homopolymers of N-vinylpyrrolidone (e.g., crospovidone, available as POLYPLASDONE XL®, ISP Technologies, Wayne, N.J.); cross-linked polymers of carboxymethylcellulose sodium (e.g., croscarmellose sodium, available as SOLUTAB®, Blanver Farmoquimica, Ltda., Cotia, Brazil; AC-DI-SOL®, FMC Corp., Philadelphia, Pa.; and VIVASOL®, J. Rettenmaier & Sohne GmbH+Co. KG Ltd., Rosenberg, Germany); cross-linked derivatives of starch (e.g., sodium starch glycolate, available as PRIMOJEL®, Campina Nederland Holding B.V., Zaltbommel, Netherland Antilles; and EXPLOTAB®, Edward Mendell Co., Inc., Carmel, N.Y.); pregelatinized starch; copolymers of methacrylic acid and divinylbenzene (e.g., polacrilex resin, available as AMBERLITE® IRP64, and polacrilin potassium, available as AMBERLITE® IRP88, Rohm and Haas, Philadelphia, Pa.); sulfonated copolymers of styrene and divinylbenzene (e.g., sodium polystyrene sulfonate, available as AMBERLITE® IRP69, and cholestyramine resin, available as DUOLITE® AP143, Rohm and Haas, Philadelphia, Pa.); and combinations thereof.

In some embodiments, a disintegrant is present in the pharmaceutical dosage forms of the present invention in a concentration of about 20% to about 60%, about 20% to about 50%, about 20% to about 40%, about 20% to about 25%, about 20% to about 30%, about 20% to about 25%, about 25% to about 60%, about 25% to about 50%, about 25% to about 40%, about 25% to about 35%, about 25% to about 30%, about 20%, about 22%, about 25%, about 27%, or about 30% by weight of the dosage forms.

In some embodiments, the pharmaceutical dosage forms further comprise a hydrophilic water-insoluble polymer that possesses wicking ability, and facilitates penetration of moisture into the dosage forms upon contact with the buccal mucosa. Hydrophilic, water-insoluble polymers suitable for use with the present invention include microcrystalline cellulose (e.g., EMCOCEL®, Penwest Pharmaceuticals Co., Patterson, N.J.; and AVICEL®, FMC Corp., Philadelphia, Pa.). In some embodiments, the hydrophilic, water-insoluble polymer suitable for use with the present invention has a bulk density of about 0.6 g/cm$^3$ or less, an apparent density of about 0.28 g/cm$^3$ to about 0.34 g/cm$^3$, and a tap density of about 0.35 g/cm$^3$ to about 0.48 g/cm$^3$. In some embodiments, a hydrophilic, water-insoluble polymer is present in the pharmaceutical dosage forms of the present invention in a concentration of about 1% to about 20%, about 1% to about 15%, about 1% to about 10%, about 1% to about 7%, about 3% to about 20%, about 3% to about 15%, about 3% to about 10%, about 3% to about 7%, about 5% to about 20%, about 5% to about 15%, about 5% to about 10%, about 3%, about 5%, about 7%, or about 10% by weight of the dosage forms.

In some embodiments, the dosage forms of the present invention comprise colloidal silicon dioxide (e.g., CAB-O-SIL®, Cabot Corp., Boston, Mass.; and AEROSIL®, Degussa AG, Frankfurt, Germany). Colloidal silicon dioxide is also known as colloidal silica, fumed silica, light anhydrous silicic acid, silicic anhydride, and silicon dioxide fumed. In some embodiments, colloidal silicon dioxide is present in the pharmaceutical dosage forms of the present invention in a concentration of about 0.1% to about 5%, about 0.1% to about 3%, about 0.2% to about 5%, about 0.2%, to about 2%, about 0.3% to about 1.5%, about 0.5%, about 0.75%, about 1%; about 1.5%, or about 2% by weight of the dosage forms.

In addition to its use as a binder and/or diluent, colloidal silicon dioxide can also function as a "glidant" to improve the flow characteristics of a powdered mixture prior to compression. Non-limiting examples of glidants suitable for use with the present invention include various forms of silicon dioxide, talc, and combinations thereof. In some embodiments, a glidant is present in the pharmaceutical dosage forms of the present invention in a concentration of 0.1% to about 5% by weight of the dosage forms.

In some embodiments, the pharmaceutical dosage forms of the present invention further comprise an inorganic excipient. Inorganic excipients suitable for use with the present invention include, but are not limited to, phosphates (e.g., calcium phosphate), sulfates (e.g., calcium sulfate), carbonates (e.g., calcium carbonate), silicates (e.g., aluminum magnesium silicate, aluminum magnesium metasilicate, aluminum silicate, bentonite, silica gel), hydrotalcites, metal hydroxides (e.g., aluminum hydroxide), metal oxides (e.g., titanium dioxide), and combinations thereof. In some embodiments, an inorganic excipient can facilitate the dispersion of the pharmaceutical dosage forms of the present invention. Not being bound by any particular theory, inorganic excipients can facilitate dispersion because they are hygroscopic and can themselves also disintegrate into smaller particles when contacted with water. Thus, when an inorganic excipient is present in the dosage forms of the present invention, a lower concentration of a disintegrant can be used. For example, an inorganic excipient can replace a portion of the disintegrant in the dosage forms of the present invention in a one-to-one manner up to about 50% by weight of the disintegrant. In some embodiments, the concentration of an inorganic excipient in the pharmaceutical dosage forms of the present invention can be determined by the concentration of the disintegrant in the dosage forms. For example, the ratio of the disintegrant to an inorganic excipient can be about 100:1 to about 1:1, about 50:1 to about 1:1, about 20:1 to about 4:1, or about 10:1 to about 5:1 by weight.

In some embodiments, the pharmaceutical dosage forms of the present invention further comprise a lubricant. As used herein, a "lubricant" refers to an excipient that can prevent adhesion of a dry composition to a surface (e.g., a surface of a mixing bowl, a compression die and/or punch), reduce interparticle friction within a substantially homogeneous powder, and aid in the ejection of a compressed dosage form from a die cavity after compression. Lubricants suitable for use with the present invention include, but are not limited to, magnesium stearate, calcium stearate, zinc stearate, sodium stearate, stearic acid, aluminum stearate, leucine, glyceryl behenate, sodium lauryl sulfate, sodium stearyl fumarate (e.g., PRUV®, Sohne GmbH & Co., Rosenberg, Germany), hydrogenated vegetable oil, and combinations thereof. In some embodiments, the lubricant is magnesium stearate, sodium stearyl fumarate, or a combination thereof. In some embodiments, a lubricant is present in the dosage forms of the present invention in a concentration of about 0.1% to about 10%, about 0.1% to about 5%, about 0.1% to about 2%, or less than about 2% by weight.

In some embodiments, the pharmaceutical dosage forms of the present invention further comprise a sweetener. Sweeteners suitable for use with the present invention have a sweet taste and are soluble in water (e.g., at least 1 part sweetener can be dissolved in about 10 parts water). Non-limiting examples of natural and artificial sweeteners suitable for use with the present invention include saccharin sodium, acesulfame potassium, altitame, aspartame, cyclamic acid and its salts (e.g., sodium cyclamate), dihydrochalcones, erythritol, fructose, glucose, glycerrhizinate, lactose, maltodextrin, mannitol, monellin, neotame, paratinose, rebulose, sorbitol, stevioside, sucralose, sucrose, thaumatin, xylitol, and combinations thereof. In some embodiments, a sweetener for use with the present invention is selected from the group consisting of saccharin, sucralose, aspartame, and combinations thereof.

In some embodiments, the pharmaceutical dosage forms of the present invention are substantially free of sugar (i.e., "sugar-free"). "Sugar-free" can also refer to a pharmaceutical dosage form that is substantially free of complex carbohydrates and/or polysaccharides that can be readily converted to sugars in the oral cavity. A sugar-free pharmaceutical dosage form can offer reduced caloric value, reduced dental caries and other dental hygienic issues, and can be preferable for administering to subjects seeking to control sugar intake (i.e., diabetic subjects). Sugar-free sweeteners suitable for use with the present invention include, but are not limited to, saccharin and salts thereof (e.g., saccharin sodium), acesulfame potassium, altitame, aspartame, cyclamic acid and its salts (e.g., sodium cyclamate), dihydrochalcones, glycerrhizinate, monellin, neotame, saccharin, stevioside, sucralose, thaumatin, and combinations thereof.

In some embodiments, the pharmaceutical dosage forms of the present invention further comprise a flavorant. As used herein, a "flavorant" refers to a natural or artificial flavoring that can be added to the pharmaceutical dosage forms to improve their taste, or to mask an unpleasant taste. Flavorants can be combined, as desired, to produce a particular flavor mixture that is compatible with a particular medication. Flavorants suitable for use with the present invention include, but are not limited to, raspberry, strawberry, cherry, almond, citrus fruit, vanilla, vanilla cream, mint, spearmint, wintergreen, grape, coconut, chocolate, menthol, licorice, butterscotch and combinations thereof. Citrus fruit flavorings suitable for use with the present invention include, but are not limited to, orange, tangerine, lemon, lime, lemon-lime, and combinations thereof.

In some embodiments a sweetener and a flavorant are present in the pharmaceutical dosage forms of the present invention in a concentration of about 7% to about 30%, about 7% to about 25%, about 7% to about 20%, about 7% to about 15%, about 10% to about 30%, about 10% to about 25%, about 10%, about 20%, about 7%, about 10%, or about 15% by weight of the dosage forms.

In some embodiments, the pharmaceutical dosage forms of the present invention further comprises a colorant. A "colorant" refers to a substance that can be added to the pharmaceutical dosage forms to enhance or modify their color or appearance. A colorant can also be added to the pharmaceutical dosage forms as a code or identifier (i.e., to indicate the manufacturer or dosage). Any type of colorant (i.e., "natural color" and/or "artificial color" such as F.D.&C. dyes) known to be "generally regarded as safe" by the FDA, and thus generally used in the confectionary trade, or otherwise approved by the FDA for use in pharmaceutical preparations, can be used with the present invention.

The pharmaceutical dosage forms of the present invention are substantially free of acids, water-soluble polymers, taste-masking polymers, and coatings. Elimination of these excipients both simplifies the manufacturing process and results in an orally disintegrating dosage form with superior disintegration characteristics. Not being bound by any particular theory, the dosage forms of the present invention are substantially free from an acid or an acidic excipient to minimize the presence of a bitter taste during administration. Because the dosage forms do not contain an acid there is no need for a polymer coating surrounding the free base clozapine granules. This simplifies the manufacturing process, and thus the present invention is also directed to a process of preparing free base clozapine orally disintegrating dosage forms by a process of dry mixing followed by direct compression.

Orally disintegrating dosage forms frequently contain a water-soluble polymer to facilitate both the absorption of moisture into the dosage form and the disintegration and/or dissolution process. Not being bound by any particular theory, the presence of a water-soluble polymer in an orally disintegrating dosage form can hinder disintegration due to the formation of a viscous gel. The dosage forms of the present invention instead comprise a non-polymeric water-soluble carrier and a hydrophilic, water-insoluble disintegrant and/or polymer. Both the hydrophilic, water-insoluble disintegrant and polymer are capable of wicking moisture into the dosage forms, and undergo rapid swelling and disintegration upon contact with moisture. Upon disintegration the non-polymeric water-soluble carrier is rapidly dissolved, imparting excellent mouth feel and taste characteristics to the dosage forms. Thus, by excluding a water-soluble polymer, the dosage forms of the present invention undergo more rapid disintegration and have appreciably better mouth feel and taste characteristics.

In some embodiments, the concentration of the non-polymeric water-soluble carrier, disintegrant, and water-insoluble polymer can be selected to optimize the physical integrity of the dosage forms of the present invention (i.e., to minimize the friability of the dosage forms of the present invention). Not being bound by any particular theory, the durability, robustness, and/or friability of the compressed dosage forms of the present invention can be estimated using the compaction index of the excipients used to prepare the dosage forms. As used herein, "compaction index" refers to the force in kiloponds (kp) required to fracture a solid mass prepared by compaction of 500 mg of powder under 1000 lbs pressure using a $^{16}/_{32}$" die and flat face punches. To obtain dosage forms having both low friability and low hardness, a mixture used to prepare the dosage forms can have a compaction index of at least about 5 kp/500 mg/1000 lbs. Not being bound by any particular theory, the compaction index can be used as an indicator of particle interactions in a compressed solid dosage form. For example, the compression of a dry mixture usually has a significant effect on the inter-particle interactions within the mixture, and can involve combinations of (i) closer contact between particles and the exclusion of air;
(ii) alignment and interlocking of particles;
(iii) the development of stresses and shearing forces that result in fracture and the generation of smaller particles;
(iv) elastic and plastic deformations of particles that can change particle shape; and
(v) chemical bonding between adjacent particles, especially during long-term storage.

Depending on the properties of the excipients comprising the mixture, powdered mixtures can undergo elastic, plastic, or visco-elastic deformation, or brittle fracture, when placed under compressive force. After compression, a compressed dosage form tends to undergo elastic recovery, visco-elastic recovery or brittle fracture. Excipients having a higher compaction index can undergo efficient compression at a minimal compressive force, and can thus produce orally disintegrating solid dosage forms that maintains their integrity during manufacturing, packaging and storage. The compaction indices for various excipients are listed in Table 1. As used herein, a "low" compaction index refers to excipients and mixtures thereof having a compaction index of about 5 kp/500 mg/1000 lbs or less, and a "high" compaction index refers to excipients and mixtures thereof having a compaction index greater than 5 kp/500 mg/1000 lbs.

TABLE 1

The compaction index of various excipients suitable for use with the present invention.

| Excipient | Compaction index (kp/500 mg/1000 lbs) |
|---|---|
| Mannitol | 9 |
| Xylitol | 0.7 |
| Crospovidone (POLYPLASDONE XL ®) | 16 |
| Croscarmellose sodium (AC-DI-SOL ®) | 6 |
| Polacrilex Resin (AMBERLITE ® IRP64) | 2 |
| Microcrystalline cellulose (AVICEL ®) | 34 |
| Aspartame | 10 |

Thus, in some embodiments excipients for use with the present invention can be selected based on their compaction index. In some embodiments, the pharmaceutical dosage forms of the present invention have a compaction index of at least about kp/500 mg/1000 lbs to about 35 kp/500 mg/1000 lbs, at least about 5 kp/500 mg/1000 lbs to about 25 kp/500 mg/1000 lbs, or at least about 5 kp/500 mg/1000 lbs to about 10 kp/500 mg/1000 lbs.

Pharmaceutical dosage forms of the present invention have a hardness and friability that makes them stable during preparation, packaging and storage. As used herein, "hardness" refers to the degree of force required to break, crumble or crack the pharmaceutical dosage forms. Hardness can be described in units of kilograms/mm$^2$ (kg/mm$^2$), pounds/in$^2$ (psi), pascals (Pa), Newtons/m$^2$ (N/m$^2$), kiloponds (kp), mohls or arbitrary units. The hardness of the pharmaceutical dosage forms can be measured, for example, using a tablet hardness tester.

In some embodiments, the pharmaceutical dosage forms of the present invention have a "low" hardness (i.e., a hardness of about 3 kp or less). The tablet hardness can be measured using, for example, a tablet hardness tester. Not being bound by any particular theory, such a low hardness can enhance water penetration into the pharmaceutical dosage forms of the present invention and facilitate their dispersion. In some embodiments, the pharmaceutical dosage forms of the present invention have a hardness of about 0.1 kp to about 5 kp, about 0.1 kp to about 3 kp, about 0.1 kp to about 2 kp, about 0.1 kp to about 1 kp, about 0.3 kp to about 5 kp, about 0.3 kp to about 3 kp, about 0.3 kp to about 2 kp, about 0.3 kp to about 1 kp, about 0.5 kp to about 5 kp, about 0.5 kp to about 3 kp, about 0.5 kp to about 2 kp, about 0.5 kp to about 1 kp, about 0.7 kp to about 5 kp, about 2 kp, or about 1 kp.

The pharmaceutical dosage forms of the present invention undergo complete disintegration without the use of effervescent agents. Suitable methods for determining the disintegration time and rate include the use of an automated disintegrating tester (e.g., available from Erweka America Corp., Annandale, N.J.) or a texture analyzer (e.g., available from Texture Technologies Corp., Scarsdale, N.Y.), and using methods described in, for example, El-Arini, S. K. and Clas S. D., "Evaluation of disintegration testing of different fast dissolving tablets using the texture analyzer," *Pharm. Dev. Technol.* 7:361-371 (2002), which is incorporated herein by reference in its entirety.

The pharmaceutical dosage forms of the present invention also have excellent "mouth feel." As used herein, "mouth feel" refers to the presence of grit or debris in the buccal cavity after the dosage form has disintegrated. Mouth feel relates to the bulkiness of the remaining tablet mass after disintegration, and can be an important parameter for maintaining patient compliance. Suitable methods for measuring mouth feel for orally disintegrating solid dosage forms of the present invention include the use blinded screening comprising administering placebo formulations to volunteer subjects, as well as using a texture analyzer. Using a texture analyzer, mouth feel is measured as the difference ($\Delta$) between the thickness (h) of a dosage form and the penetration distance (d) of water or liquid into the dosage form. Mouth feel improves as the value $\Delta$ is minimized.

Orally disintegrating tablets containing free base clozapine can be manufactured using dry mixing followed by direct compression. Methods of tablet formulation have been developed in order to impart desirable characteristics to the drug/material(s) to be compressed into a solid dosage form. Usually, the material to be compressed into a solid dosage form includes one or more excipients to impart free-flowing, lubrication, and cohesive properties to the drug(s) that is to be formulated into a dosage form. Typically, excipients are added to the formulation to impart good flow and compression characteristics to the mixture that is compressed. Such properties are typically imparted to these excipients via a pre-processing step such as wet granulation, slugging, spray drying, spheronization, or crystallization. Useful direct compression excipients include processed forms of cellulose, sugars, and dicalcium phosphate dihydrate, among others.

The in vivo concentration of clozapine and its metabolites, as well as pharmacokinetic parameters can be determined by sampling the blood plasma of a subject after administration of the pharmaceutical dosage forms of the present invention. The non-effervescent, orally disintegrating solid pharmaceutical dosage forms of the present invention have excellent bioavailability. In some embodiments, the pharmaceutical dosage forms of the present invention have a bioavailability substantially equivalent to traditional oral dosage forms (e.g., oral tablets or oral solutions) containing clozapine in a substantially equivalent dose (i.e., the pharmaceutical dosage forms of the present invention have a substantially equivalent $AUC_{inf}$). As used herein, "$AUC_{inf}$" refers to the Area Under the Concentration time curve, wherein the last concentration is extrapolated to baseline based on the rate constant for elimination. While it is possible that some portion of the free base clozapine contained with the dosage forms of the present invention can be absorbed by the buccal mucosa, the primary pathway by which clozapine is absorbed is through the GI tract.

In some embodiments, the bioavailability (i.e., $AUC_{inf}$) of clozapine administered from the pharmaceutical dosage forms of the present invention is substantially equivalent to that observed upon administration of a presently available oral dosage form (e.g., FAZACLO® orally disintegrating tablets) that contain an equivalent dose of free base clozapine.

Processes to Prepare the Dosage Forms

The present invention is also directed to a process of preparing non-effervescent, orally disintegrating solid pharmaceutical dosage forms, the process comprising:

(a) dry mixing:
(i) free base clozapine,
(ii) a non-polymeric, water-soluble carrier, and
(iii) a disintegrant, to form a dry mixture, wherein the disintegrant is present in a concentration of about 20% to about 60% by weight of the dry mixture; and (b) compressing the dry mixture to form the pharmaceutical dosage forms, wherein the dry mixture is substantially free of: acids, water-soluble polymers, taste-masking polymers, and coatings, and wherein the dosage forms disintegrate in about 60 seconds or less.

The present invention is also directed to dosage forms prepared by the above process.

The dosage forms of the present invention are advantageously prepared by a direct mixing process that forgoes the need to use more complicated wet granulation, milling, and fluid-bed drying processes. The present process also avoids the use of costly lyophilization processes.

The present invention also permits a great deal of latitude regarding the order in which clozapine is mixed with the various excipients to form a dry mixture. In some embodiments, free base clozapine is first mixed with the water-insoluble excipients (i.e., a disintegrant and optionally a hydrophilic, water-insoluble polymer), and then a non-polymeric, water-soluble carrier is added. Other excipients such as, but not limited to, a flavorant and a sweetener can be added to the dry mixture at any time during the mixing process.

In some embodiments, the process further comprises one or more screening or sizing steps to ensure that the dry mixture has a uniform particle size distribution.

In some embodiments, a lubricant and/or glidant are added to the dry mixture immediately before direct compression. The lubricated dry mixture is then compressed to form non-effervescent, orally disintegrating solid dosage forms using compression means known to those of ordinary skill in the art of manufacturing solid dosage forms. The compressed dosage forms are then packaged in, for example, a resealable container or a peelable blister package.

Methods of Treatment

The present invention is also directed to a method of treating schizophrenia or dopamine mediated behaviors comprising administering non-effervescent, orally disintegrating solid pharmaceutical dosage forms to a subject in need thereof, wherein the pharmaceutical dosage forms comprise: a substantially homogeneous compressed dry mixture comprising:

(a) free base clozapine;
(b) a non-polymeric, water-soluble carrier; and
(c) a disintegrant in a concentration of about 20% to about 60% by weight of the dosage forms;

wherein the dry mixture and pharmaceutical dosage forms are substantially free of: acids, water-soluble polymers, taste-masking polymers, and coatings, and wherein the dosage forms disintegrate without in about 60 seconds or less.

The non-effervescent, orally disintegrating, dosage forms of the present invention are useful in the therapeutic treatment for patients suffering from schizophrenia, acute manic episodes associated with Bipolar I Disorder, and related conditions. The free base clozapine compositions of the present invention may be administered alone or in conjunction with other medications or pharmaceutical compositions. The invention is directed to a method of treating and or preventing diseases in a human subject by administration of the free base clozapine orally disintegrating dosage forms of the present invention.

The terms "treat" and "treatment" refer to both therapeutic treatment and prophylactic, maintenance, or preventative measures, wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms or signs; diminishment of extent of condition, disorder or disease; stabilization (i.e., not worsening) of the state of condition, disorder or disease; delay in onset or slowing of condition, disorder or disease progression; amelioration of the condition, disorder or disease state, remission (whether partial or total), whether detectable or undetectable; or enhancement or improvement of condition, disorder or disease. Treatment includes eliciting a clinically significant response, without excessive levels of side effects. Treatment also includes prolonging survival as compared to expected survival if not receiving treatment.

The pharmaceutical dosage forms of the present invention can be administered alone or in conjunction with other anti-psychotic and atypical anti-psychotic medications. In some embodiments, the present invention is directed to a method of treating and or preventing diseases and alleviating symptoms of schizophrenia and/or psychosis in a human subject by administering the free base clozapine pharmaceutical dosage forms of the present invention.

As used herein, "administering to" refers to placing a pharmaceutical dosage form of the present invention in physical contact with the buccal cavity (i.e., the tongue, the buccal mucosa, the sublingual mucosa, etc.) of a subject in need thereof.

The dosage forms of the present invention are useful in the therapeutic treatment for patients suffering from schizophrenia. In addition, the disclosed free base clozapine compositions can be used to treat other disorders and diseases currently being treated by known antipsychotic and atypical antipsychotic active agents.

In some embodiments, the present invention is directed to a method of administering free base clozapine to a diabetic subject, the method comprising administering to a diabetic subject a pharmaceutical dosage form of the present invention.

The following examples of processing conditions and parameters are given for the purpose of illustrating the present invention and shall not be construed as being limitations on the scope or spirit of the invention.

EXAMPLES

Example 1

The particle size and particle size distribution of the various excipient used in the particulate mixture of the present invention are listed in Table 2.

TABLE 2

Ingredients and their particle size distributions used to prepare the non-effervescent, orally disintegrating solid pharmaceutical dosage forms of the present invention (Dosage Form A).

| Ingredient | $D_{10}$ (μm) | $D_{50}$ (μm) | $D_{90}$ (μm) | VMD (μm) |
|---|---|---|---|---|
| Mannitol, USP (PARTECK ® M200) | 81 | 221 | 507 | 263 |
| Xylitol (XYLISORB ® 300) | 86 | 167 | 310 | 184 |
| Crospovidone, NF (POLYPLASDONE XL ®) | 20 | 68 | 233 | 101 |
| Microcrystalline cellulose, NF (AVICEL ® PH-101) | 21 | 50 | 105 | 57 |
| Free base clozapine | 5 | 19 | 51 | 25 |

Example 2

Non-effervescent, orally disintegrating solid pharmaceutical dosage forms of the present invention (Dosage Form A) were prepared by the process of FIG. 1 using the ingredients and amounts listed in Table 3.

Free base clozapine, a disintegrant (e.g., crospovidone), and a hydrophilic, water-insoluble polymer were screened and mixed in a bin blender for 10 minutes. A non-polymeric water-soluble carrier was screened (e.g., mannitol and xylitol) and placed in the bin blender and mixed for an additional 10 minutes. Finally a sweetener and flavorant were added to the bin blender followed by additional mixing. The resulting mixture was sized using a #20 mesh screen, mixed, lubricated, and then compressed into tablets using a tablet press.

TABLE 3

Ingredients and their amounts used to prepare a pharmaceutical dosage form of the present invention.

| Ingredients | Purpose | 150 mg Tablet | 300 mg Tablet | 600 mg Tablet | % (w/w) |
|---|---|---|---|---|---|
| Clozapine | Active agent | 25 | 50 | 100 | 16.7 |
| Mannitol, USP (PARTECK ® M200) | Non-polymeric, water-soluble carrier | 63 | 126 | 252 | 42 |
| Xylitol (XYLISORB ® 300) | | 10 | 20 | 40 | 6.7 |
| Crospovidone, NF (POLYPLASDONE XL ®) | Disintegrant | 35 | 70 | 140 | 23.3 |
| Microcrystalline cellulose, NF (AVICEL ® PH-101) | Hydrophilic, water-insoluble polymer | 6.5 | 13 | 26 | 4.3 |
| Colloidal silicon dioxide, NF (CAB-O-SIL ®) | Glidant | 1.9 | 3.8 | 7.6 | 1.3 |
| Peppermint flavor (SN302419) | Flavorant | 1 | 2 | 4 | 0.7 |
| Aspartame powder, USP (NUTRASWEET ® Powder) | Sweetener | 5 | 10 | 20 | 3.3 |
| Magnesium stearate, NF | Lubricant | 1.3 | 2.6 | 5.2 | 0.9 |
| Sodium stearyl fumarate, NF | | 1.3 | 2.6 | 5.2 | 0.9 |
| TOTAL | | 150 mg | 300 mg | 600 mg | 100% |

All of the various embodiments or options described herein can be combined in any and all variations. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A non-effervescent, orally disintegrating solid pharmaceutical dosage form comprising a substantially homogeneous compressed dry mixture comprising:
    (a) free base clozapine;
    (b) a non-polymeric, water-soluble carrier;
    (c) a hydrophilic water-insoluble polymer in a concentration of 1% to 20% by weight of the dosage form; and
    (d) a disintegrant in a concentration of 20% to 60% by weight of the dosage form, wherein the disintegrant is selected from the group consisting of:
        crospovidone, croscarmellose sodium, sodium starch glycolate, and combinations thereof;
    wherein the dry mixture and pharmaceutical dosage form are free of:
        acids, water-soluble polymers, taste-masking polymers, and coatings, and wherein the dosage foam disintegrates in about 60 seconds or less.

2. The pharmaceutical dosage form of claim 1, wherein the free base clozapine is present in a concentration of about 10% to about 30% by weight of the dosage form.

3. The pharmaceutical dosage form of claim 1, wherein the free base clozapine has a particle size $D_{50}$ of about 20 μm or less.

4. The pharmaceutical dosage form of claim 1, wherein the free base clozapine has a particle size $D_{90}$ of about 50 μm or less.

5. The pharmaceutical dosage form of claim 1, wherein the non-polymeric, water-soluble carrier is selected from the group consisting of: arabinose, dextrose, erythritol, fructose, galactose, inositol, lactitol, maltitol, maltose, mannitol, sorbitol, sucrose, tagatose, trehalose, xylitol, and combinations thereof.

6. The pharmaceutical dosage form of claim 1, wherein the non-polymeric, water-soluble carrier is present in a concentration of about 20% to about 60% by weight of the dosage form.

7. The pharmaceutical dosage form of claim 1, further comprising: a flavorant and a sweetener in a concentration of about 7% to about 30% by weight of the dosage form.

8. The pharmaceutical dosage form of claim 1, wherein the pH of the dry mixture is about 6.5 to about 8.

9. The pharmaceutical dosage form of claim 1, wherein the non-polymeric, water-soluble carrier is present in a concentration of about 1% to about 10% by weight of the dosage form.

10. The pharmaceutical dosage form of claim 1, wherein the non-polymeric, water-soluble carrier is present in a concentration of about 3% to about 10% by weight of the dosage form.

11. The pharmaceutical dosage form of claim 1, wherein the disintegrant is present in a concentration of 25% to 60% by weight of the dosage form.

12. The pharmaceutical dosage form of claim 1, wherein the disintegrant is present in a concentration of 25% to 50% by weight of the dosage form.

13. A method of treating schizophrenia comprising administering a non-effervescent, orally disintegrating solid pharmaceutical dosage form to a subject in need thereof, wherein the pharmaceutical dosage form comprises: a substantially homogeneous compressed dry mixture comprising:
    (a) free base clozapine;
    (b) a non-polymeric, water-soluble carrier;
    (c) a hydrophilic water-insoluble polymer in a concentration of 1% to 20% by weight of the dosage form; and
    (d) a disintegrant in a concentration of 20% to 60% by weight of the dosage form, wherein the disintegrant is selected from the group consisting of:
        crospovidone, croscarmellose sodium, sodium starch glycolate, and combinations thereof;
    wherein the dry mixture and pharmaceutical dosage form are substantially free of:
        acids, water-soluble polymers, taste-masking polymers, and coatings, and wherein the dosage form disintegrates in about 60 seconds or less.

14. The method of claim 13, wherein the free base clozapine has a particle size $D_{50}$ of about 20 μm or less.

15. The method of claim 13, wherein the free base clozapine has a particle size $D_{90}$ of about 50 μm or less.

16. The method of claim 13, wherein the substantially homogeneous compressed dry mixture further comprises a flavorant and a sweetener in a concentration of about 7% to about 30% by weight of the dry mixture.

17. The method of claim 13, wherein the non-polymeric, water-soluble carrier is present in a concentration of about 1% to about 10% by weight of the dosage form.

18. The method of claim 13, wherein the non-polymeric, water-soluble carrier is present in a concentration of about 3% to about 10% by weight of the dosage form.

19. The method of claim 13, wherein the disintegrant is present in a concentration of 25% to 60% by weight of the dosage form.

20. The method of claim 13, wherein the disintegrant is present in a concentration of 25% to 50% by weight of the dosage form.

21. A process of preparing a non-effervescent, orally disintegrating solid pharmaceutical dosage form, the process comprising:
    (a) dry mixing:
        (i) free base clozapine,
        (ii) a non-polymeric, water-soluble carrier,
        (iii) a hydrophilic water-insoluble polymer in a concentration of 1% to 20% by weight of the dosage form; and
        (iv) a disintegrant selected from the group consisting of: crospovidone, croscarmellose sodium, sodium starch glycolate, and combinations thereof,
        to form a dry mixture, wherein the disintegrant is present in a concentration of 20% to 60% by weight of the dry mixture; and
    (b) compressing the dry mixture to form the pharmaceutical dosage form, wherein the dry mixture is substantially free of: acids, water-soluble polymers, taste-masking polymers, and coatings, and
    wherein the dosage form disintegrates in about 60 seconds or less.

22. The process of claim 21, further comprising adding to the dry mixture a flavorant and a sweetener in a concentration of about 7% to about 30% by weight of the dry mixture.

23. The process of claim 21, wherein the free base clozapine has a particle size $D_{50}$ of about 20 μm or less.

24. The process of claim 21, wherein the free base clozapine has a particle size $D_{90}$ of about 50 μm or less.

25. A pharmaceutical dosage form prepared by the process of claim 21.

26. The process of claim 21, wherein the non-polymeric, water-soluble carrier is present in a concentration of about 1% to about 10% by weight of the dosage form.

27. The process of claim 21, wherein the non-polymeric, water-soluble carrier is present in a concentration of about 3% to about 10% by weight of the dosage form.

28. The process of claim 21, wherein the disintegrant is present in a concentration of 25% to 60% by weight of the dosage form.

29. The process of claim 21, wherein the disintegrant is present in a concentration of 25% to 50% by weight of the dosage form.

* * * * *